United States Patent [19]

Nezu et al.

[11] Patent Number: 4,770,691
[45] Date of Patent: Sep. 13, 1988

[54] 2-(4',6'-DI-SUBSTITUTED PYRIMIDINE-2'-YL)OXY- OR THIO-BENZOIC ACID

[75] Inventors: Yukio Nezu, Fujieda; Kazuhiko Sugiyama, Shizuoka; Shoji Kusano, Hamamatsu; Yasufumi Toyokawa; Takeshige Miyazawa, both of Shizuoka; Ikuo Kajiwara, Nagaokakyo, all of Japan

[73] Assignees: Kumiai Chemical Industry Co., Ltd.; Ihara Chemical Industry Co., Ltd., both of Tokyo, Japan

[21] Appl. No.: 918,925

[22] Filed: Oct. 15, 1986

[30] Foreign Application Priority Data

Oct. 15, 1985 [JP] Japan ............................ 60-229636

[51] Int. Cl.$^4$ .................... A01N 43/54; C07D 239/28
[52] U.S. Cl. ............................ 71/92; 544/300; 544/310; 544/312; 544/313; 544/317
[58] Field of Search .............. 544/305, 313, 314, 315, 544/316, 300, 310, 312, 317; 71/92

[56] References Cited

U.S. PATENT DOCUMENTS 4,427,437  1/1984  Serban et al. .................... 544/315

FOREIGN PATENT DOCUMENTS

| 1187 | 3/1979 | European Pat. Off. . |
| 2148667 | 9/1971 | Fed. Rep. of Germany . |
| 429474 | 5/1967 | Japan . |
| 54-55729 | 5/1979 | Japan . |
| 54-117486 | 9/1979 | Japan . |

OTHER PUBLICATIONS

Serban, CA 92-175773f.

Abstract of JP55-115873, 9/80.
Patent Abstracts of Japan, vol. 4, No. 174 (C-33)[656], Dec. 2, 1980; & JP-A-55 115 873 (Sankyo K.K.) 06-0-9-1980.
Agr. Biol. Chem., vol. 30, No. 9, pp. 896-905, 1966, "Syntheses and Herbicidal Activities of Phenoxypyrimidines and Phenoxytriazines" by Teruomi Jojima et al; received Feb. 28, 1966.

Primary Examiner—Donald G. Daus
Assistant Examiner—Cecilia Shen
Attorney, Agent, or Firm—Oblon, Fisher, Spivak, McClelland & Maier

[57] ABSTRACT

As new compounds are provided 2-(4',6'-di-substituted pyrimidine-2'-yl)oxy- or thio-benzoic acid derivatives of the formula

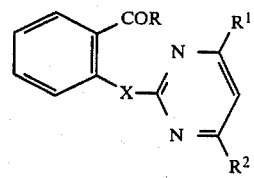

wherein R is hydrogen, hydroxy, alkoxy, alkenyloxy, alkylthio or other substituents, $R^1$ and $R^2$ are each a halo, alkyl, alkoxy or other substituents; and X is oxygen or sulfur atom. These new compounds are useful as herbicidal agent effective to inhibit the growth of annual weeds and also perennial weeds predominant in irrigated fields of aquatic rice plants and in plowed fields.

20 Claims, No Drawings

2-(4',6'-DI-SUBSTITUTED PYRIMIDINE-2'-YL)OXY- OR THIO-BENZOIC ACID

SUMMARY OF THE INVENTION

This invention relates to new pyrimidine derivatives useful as a herbicidal agent and, more particularly, to new 2-(4',6'-di-substituted pyrimidine-2'-yl)oxy- or thiobenzoic acid derivatives which are useful as a herbicidal agent to inhibit the growth of annual weeds and also the growth of perennial weeds. This invention also relates to a herbicidal composition comprising as active ingredient said new pyrimidine derivative, which is applicable to the herbicidal treatments of aquatic rice plant fields, plowed fields and non-farm lands where various kinds of weeds have grown. This invention further relates to a method of combating or killing weeds by application of said new pyrimidine derivative.

BACKGROUND OF THE INVENTION

In recent years, many kinds of herbicidal agents have been provided and used in practice and have made great contributions in reducing the labor power or works in the agriculture and in improving the yields of the agricultural products.

Still, most of the known herbicidal agents are not completely satisfactory but can show some problems in respect of their herbicidal effects and their safety to man and phyto-toxicity to crop plants upon the actual application to the agricultural fields. For instance, perennial weeds such as purple nutsedge (*Cyperus rotundus*) and Johnson grass (*Sorghum halepense*) grow widely in the agricultural fields over the world, and it is known that these perennial weeds are difficult to be controlled or killed. Accordingly, many kinds of herbicidal agents have been provided and applied to combat or control the growth of perennial weeds. However, these known herbicidal agents or compounds which have been employed for control of the perennial weeds are not yet entirely satisfactory, since their herbicidal effects are not necessarily sound and their phyto-toxicity to the crop plants are sometimes objectionable. In these circumstances, the demand for new herbicidal agents having more improved properties is lasting. In particular, as herbicidal compounds containing a pyrimidine nucleus is known 2-(3'-bromo-phenoxy)-5-chloropyrimidine (see Japanese patent application (unexamined) first publication "Kokai" No. 55729/79 corresponding to U.S. Pat. No. 4,427,437). This particular herbicidal compound can show such drawback that its herbicidal activity is low against the above-mentioned perennial weeds, including purple nutsedge and Johnson grass.

In an attempt to provide such new herbicidal compounds which are effective to combat or kill not only the annual weeds but also the perennial weeds, we, the present inventors, have made our extensive researches on 2-phenoxypyrimidine derivatives. As a result, we have succeeded in synthetizing a class of new 2-phenoxypyrimidines having some substituents introduced at the specific positions of the pyrimidine ring and the benzene ring thereof, which are represented by the general formula (I) given hereinafter. We have now found that the new 2-phenoxy-pyrimidine derivatives of the general formula (I) now synthetized are able to exhibit high herbicidal activities not only to a wide variety of annual weeds but also to a variety of perennial weeds, including purple nutsedge and Johnson grass, and also that the new compounds of the formula (I) are of no or little phyto-toxicity to many kinds of crop plants and can be applied to the agricultural fields with very much high safety, so that the new compounds of the formula (I) are useful as a herbicidal agent having the unexpectably excellent properties.

DETAILED DESCRIPTION OF THE INVENTION

According to a first aspect of this invention, therefore, there is provided a pyrimidine derivative of the general formula (I)

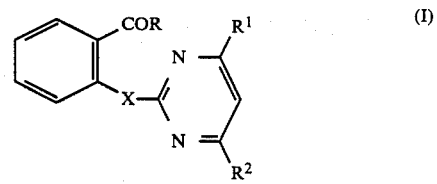

wherein R denotes a hydrogen atom or a hydroxy group or a lower alkoxy group, a lower alkylthio group, a lower alkenyloxy group, a lower alkynyloxy group, a phenoxy group, a chlorophenoxy group, an alkylphenoxy group, a di-lower-alkylphenoxy group, a lower-alkoxyphenoxy group, a phenylthio group, an isopropylideneaminoxy group, an imidazolyl group, a group of the formula —O—$(CH_2)_n$—$R^3$ where $R^3$ is a halogen atom or a hydroxy group, a trifluoromethyl group, a lower alkoxy group, a lower alkylthio group, a lower alkylsulfonyl group, a lower alkoxycarbonyl group, a lower alkylcarbonyl group, a phenyl group or a furyl group; and n is an integer of 1 or 2, or R denotes a group —OM where M is a cation of an alkali metal or alkaline earth metal, ammonium cation or an organic substituted ammonium cation, and $R^1$ and $R^2$ are the same or different and each denotes a halogen atom or a lower alkyl group, a lower haloalkyl group, a lower alkoxy group, a lower alkylthio group, a mono, di- or tri-halo-lower-alkoxy group, a di-lower-alkylamino group, a methanesulfonylmethyl group, a trifluoromethylphenoxyphenoxy group, a methylphenoxy group or a dimethylphenoxy group, and X is an oxygen atom or sulfur atom.

In accordance with this invention, by the term "lower alkyl", including the same term occurring in such terms as "lower alkylthio group", "lower alkylsulfonyl group", "lower alkylcarbonyl group", "lower haloalkyl group" and "di-lower-alkylamino group", is meant an alkyl group containing 1 to 6 carbon atoms, and preferably an alkyl group containing 1 to 4 carbon atoms. Thus, the term "lower alkyl group" includes a linear or branched alkyl group such as methyl, ethyl, n-propyl, isopropyl, n-butyl, isobutyl, tert.-butyl, n-pentyl, isopentyl, n-hexyl, isohexyl and others. By the term "lower alkoxy group" is meant an alkoxy group of 1 to 6 carbon atoms, preferably 1 to 4 carbon atoms, such as methoxy, ethoxy, n-propoxy, isopropoxy, n-butoxy, tert-butoxy and n-hexyloxy. By the term "lower alkenyloxy group" is meant an alkenyloxy group containing 2 to 6 carbon atoms, preferably 2 to 4 carbon atoms, such as allyloxy, n-propenyloxy, n-butenyloxy and hexenyloxy. By the term "lower alkynyloxy group" is meant an alkynyloxy group containing 2 to 6 carbon atoms, preferably 1 to 4 carbon atoms, such as ethynyloxy, propynyloxy, butynyloxy and hexynyloxy.

The "halogen" includes chlorine, bromine, iodine and fluorine. The "alkali metal" includes sodium, potassium and lithium, and the "alkaline earth metal" includes calcium and magnesium.

By the term "an organic substituted ammonium cation" is meant such cation of the formula [—NR$^9$R$^{10}$R$^{11}$R$^{12}$]+ wherein R$^9$, R$^{10}$, R$^{11}$ and R$^{12}$ are each a hydrogen atom, a linear or branched (C$_1$-C$_6$) alkyl group such as methyl, ethyl, n-propyl, isopropyl, n-butyl; a (C$_1$-C$_6$) hydroxyalkyl group; phenyl group or benzyl group. A suitable example of the organic substituted ammonium cation is [—NH$_3$—C$_3$H$_7$—i]+.

Particular examples of the new compound of the formula (I) according to this invention are listed in Table 1 below, together with their physical constants. Compound Numbers given in Table 1 are referred to in the following descriptions to identify the compound as used or tested, except otherwise stated.

TABLE 1

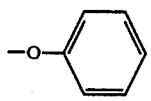
(I)

| Compound No. | R | X | R$^1$ | R$^2$ | Melting point or refractive index |
|---|---|---|---|---|---|
| 1 | H | O | Cl | OCH$_3$ | mp. 88–90° C. |
| 2 | H | O | OCH$_3$ | OCH$_3$ | mp. 60–63° C. |
| 3 | OH | O | Cl | OCH$_3$ | mp. 149–152° C. |
| 4 | OH | O | OCH$_3$ | OCH$_3$ | mp. 150–152° C. |
| 5 | OH | S | OCH$_3$ | OCH$_3$ | mp. 127–130° C. |
| 6 | OCH$_3$ | O | Cl | OCH$_3$ | mp. 54–55° C. |
| 7 | OC$_2$H$_5$ | O | Cl | OCH$_3$ | $n_D^{20}$ 1.5609 |
| 8 | OC$_3$H$_7$—i | O | Cl | OCH$_3$ | $n_D^{20}$ 1.5505 |
| 9 | OCH$_3$ | O | Cl | CH$_3$ | $n_D^{20}$ 1.5682 |
| 10 | OCH$_3$ | S | Cl | OCH$_3$ | mp. 57–59° C. |
| 11 | OCH$_3$ | S | OCH$_3$ | OCH$_3$ | $n_D^{20}$ 1.5934 |
| 12 | OCH$_3$ | O | F | OCH$_3$ | $n_D^{20}$ 1.5470 |
| 13 | OCH$_3$ | O | OCHF$_2$ | OCH$_3$ | $n_D^{20}$ 1.5228 |
| 14 | OCH$_3$ | O | —N(CH$_3$)$_2$ | OCH$_3$ | mp. 79–81° C. |
| 15 | OCH$_3$ | O | —SCH$_3$ | OCH$_3$ | mp. 58–60° C. |
| 16 | OCH$_3$ | O | CH$_3$ | OCH$_3$ | $n_D^{20}$ 1.5561 |
| 17 | OCH$_3$ | O | OCH$_3$ | OCH$_3$ | mp. 105–106° C. |
| 18 | OC$_2$H$_5$ | O | OCH$_3$ | OCH$_3$ | $n_D^{20}$ 1.5411 |
| 19 | OC$_3$H$_7$—n | O | OCH$_3$ | OCH$_3$ | $n_D^{20}$ 1.5382 |
| 20 | OC$_3$H$_7$—i | O | OCH$_3$ | OCH$_3$ | $n_D^{20}$ 1.5350 |
| 21 | OC$_4$H$_9$—n | O | OCH$_3$ | OCH$_3$ | $n_D^{20}$ 1.5339 |
| 22 | OCH$_3$ | O | OCH$_3$ | OC$_2$H$_5$ | $n_D^{20}$ 1.5465 |
| 23 | OCH$_3$ | O | OCH$_3$ | OC$_3$H$_7$—i | $n_D^{20}$ 1.5382 |
| 24 | OCH$_3$ | O | CH$_3$ | CH$_3$ | $n_D^{20}$ 1.5603 |
| 25 | SC$_2$H$_5$ | O | OCH$_3$ | OCH$_3$ | mp. 75–77° C. |
| 26 | —OCH$_2$CH=CH$_2$ | O | OCH$_3$ | OCH$_3$ | $n_D^{20}$ 1.5510 |
| 27 | —OCH$_2$C≡CH | O | OCH$_3$ | OCH$_3$ | mp. 88–90° C. |
| 28 | 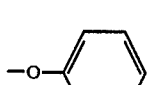 | O | Cl | OCH$_3$ | mp. 74–76° C. |
| 29 | 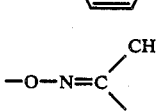 | O | OCH$_3$ | OCH$_3$ | $n_D^{20}$ 1.5841 |
| 30 | —O—N=C(CH$_3$)$_2$ | O | OCH$_3$ | OCH$_3$ | mp. 119° C. |
| 31 | 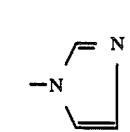 | O | Cl | OCH$_3$ | $n_D^{20}$ 1.6006 |

TABLE 1-continued (I)

[Structure: phenyl ring with COR substituent, linked via X to pyrimidine ring bearing R¹ and R²]

| Compound No. | R | X | R¹ | R² | Melting point or refractive index |
|---|---|---|---|---|---|
| 32 | [imidazol-1-yl] | O | OCH₃ | OCH₃ | $n_D^{20}$ 1.5881 |
| 33 | —OC₂H₄Cl | O | OCH₃ | OCH₃ | $n_D^{20}$ 1.5565 |
| 34 | —OC₂H₄OH | O | OCH₃ | OCH₃ | $n_D^{20}$ 1.5585 |
| 35 | —OC₂H₄OCH₃ | O | OCH₃ | OCH₃ | $n_D^{20}$ 1.5434 |
| 36 | —OC₂H₄SCH₃ | O | OCH₃ | OCH₃ | $n_D^{20}$ 1.5641 |
| 37 | —OCH₂SCH₃ | O | OCH₃ | OCH₃ | $n_D^{20}$ 1.5688 |
| 38 | —OC₂H₄SO₂CH₃ | O | OCH₃ | OCH₃ | mp. 132–134° C. |
| 39 | —OCH₂SO₂CH₃ | O | OCH₃ | OCH₃ | $n_D^{20}$ 1.5600 |
| 40 | —OCH₂COC₂H₅ (ketone) | O | OCH₃ | OCH₃ | $n_D^{20}$ 1.5385 |
| 41 | —OCH₂CCH₃ (ketone) | O | OCH₃ | OCH₃ | $n_D^{20}$ 1.5535 |
| 42 | —OCH₂-phenyl | O | Cl | OCH₃ | $n_D^{20}$ 1.5919 |
| 43 | —OCH₂-phenyl | O | OCH₃ | OCH₃ | $n_D^{20}$ 1.5780 |
| 44 | —ONa | O | Cl | OCH₃ | mp. 196–200° C. (dec.) |
| 45 | —ONa | O | OCH₃ | OCH₃ | mp. 253–259 (dec.) |
| 46 | —O.H₃N—C₃H₇—i | O | OCH₃ | OCH₃ | mp. 125–131° C. |
| 47 | O.½ Ca | O | OCH₃ | OCH₃ | mp. 149–155° C. |
| 48 | —OCH₂CF₃ | O | OCH₃ | OCH₃ | $n_D^{20}$ 1.5129 |
| 49 | —OCH₃ | O | OCH₃ | CH₂F | $n_D^{20}$ 1.5485 |
| 50 | —OH | O | OCH₃ | CH₂F | mp. 120–122° C. |
| 51 | —O-(4-Cl-phenyl) | O | OCH₃ | OCH₃ | mp. 84–85° C. |
| 52 | —O-(4-CH₃-phenyl) | O | OCH₃ | OCH₃ | mp. 102–103° C. |
| 53 | —O-(2-CH₃-phenyl) | O | OCH₃ | OCH₃ | $n_D^{20}$ 1.5782 |

TABLE 1-continued $$\text{(I)}$$

Structure: phenyl with COR substituent and X-linked to pyrimidine bearing $R^1$ and $R^2$.

| Compound No. | R | X | $R^1$ | $R^2$ | Melting point or refractive index |
|---|---|---|---|---|---|
| 54 | —O—(2,6-dimethylphenyl) | O | $OCH_3$ | $OCH_3$ | mp. 100–101° C. |
| 55 | —O—(2-methoxyphenyl) | O | $OCH_3$ | $OCH_3$ | mp. 120–122° C. |
| 56 | —O—(2-chlorophenyl) | O | $OCH_3$ | $OCH_3$ | mp. 73–75° C. |
| 57 | —S—phenyl | O | $OCH_3$ | $OCH_3$ | $n_D^{20}$ 1.6203 |
| 58 | —O—(4-n-octylphenyl) | O | $OCH_3$ | $OCH_3$ | $n_D^{20}$ 1.5524 |
| 59 | —OCH$_2$—(furan-2-yl) | O | $OCH_3$ | $OCH_3$ | $n_D^{20}$ 1.5655 |
| 60 | —OCH$_3$ | O | $OCHF_2$ | $OCHF_2$ | $n_D^{20}$ 1.4968 |
| 61 | —OH | O | $OCHF_2$ | $OCHF_2$ | mp. 107–109° C. |
| 62 | —OCH$_2$—phenyl | O | $OCHF_2$ | $OCHF_2$ | $n_D^{20}$ 1.5215 |
| 63 | $OCH_3$ | O | $OCH_3$ | —O—phenyl—O—(3-CF$_3$-phenyl) | $n_D^{20}$ 1.5659 |
| 64 | $OCH_3$ | O | $OCH_3$ | —O—(2-methylphenyl) | $n_D^{20}$ 1.5750 |

TABLE 1-continued (I)

| Compound No. | R | X | $R^1$ | $R^2$ | Melting point or refractive index |
|---|---|---|---|---|---|
| 65 | OCH$_3$ | O | OCH$_3$ | (3-methylphenoxy) | $n_D^{20}$ 1.5790 |
| 66 | OCH$_3$ | O | OCH$_3$ | (2,6-dimethylphenoxy) | $n_D^{20}$ 1.5605 |

According to particular embodiments of the first aspect of this invention, amongst the new compounds of the formula (I), there are provided eleven classes of the compounds represented respectively by the formula (I') and the formula (Ia) to (Ij) as shown below.

(1) A compound of the formula (I')

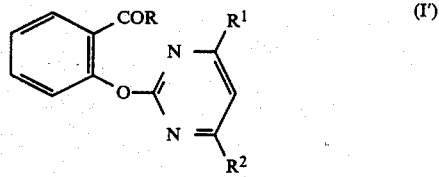

wherein R is a hydrogen atom or a hydroxy group, a lower alkoxy group, a lower alkylthio group, a lower alkenyloxy group, a lower alkynyloxy group, a phenoxy group or a group of the formula —O—(CH$_2$)$_n$—R$^3$ where R$^3$ is a halogen atom, a hydroxy group, a lower alkoxy group, a lower alkylthio group, a lower alkylsulfonyl group, a lower alkoxycarbonyl group, a lower alkylcarbonyl group, or a phenyl group; and n is an integer of 1 or 2; or R is a group of the formula —OM where M is a cation of an alkali metal or an alkaline earth metal; or ammonium cation or an organic substituted ammonium cation, and $R^1$ and $R^2$ are each a halogen atom or a lower alkyl group, a lower alkoxy group, a lower alkylthio group, a halolower-alkoxy group or a di-lower-alkylamino group.

(2) A compound of the formula (Ia)

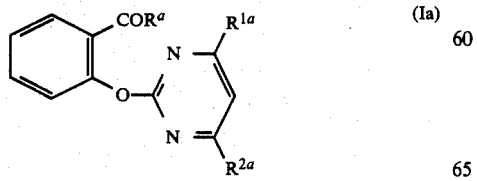

wherein $R^a$ is a hydroxy group, a lower alkoxy group, a lower alkenyloxy group, a lower alkynyloxy group or a group of the formula —OM where M is a cation of an alkali metal, an alkaline earth metal or an ammonium cation; and $R^{1a}$ and $R^{2a}$ are each a lower alkoxy group.

(3) A compound of the formula (Ib)

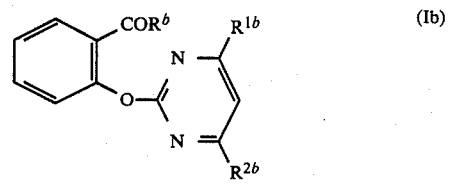

wherein $R^b$ is a hydroxy group or a lower alkoxy group; $R^{1b}$ is a halogen atom, particularly chlorine or fluorine atom, or a lower alkyl group, or a di-fluoro-lower alkoxy group, and $R^{2b}$ is a lower alkyl group or a lower alkoxy (4) A compound of the formula (Ic)

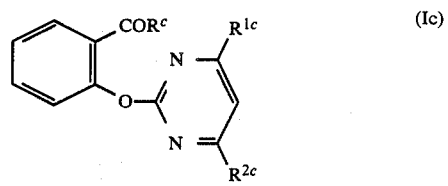

wherein $R^c$ is a lower alkoxy group, $R^{1c}$ is a di-loweralkylamino group or a lower alkylthio group, and $R^{2c}$ is a lower alkoxy group.

(5) A compound of the formula (Id)

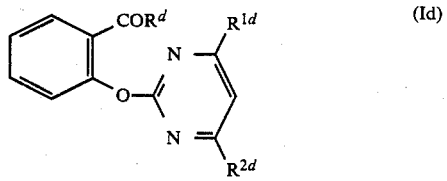

wherein $R^d$ is a lower alkylthio group, a phenoxy group, an isopropylideneaminoxy group, an imidazolyl group, or a group of the formula —O—(CH$_2$)$_n$—R$^3$ where R$^3$ is a halogen atom or a hydroxy group, a lower alkoxy group, a lower alkylthio group, a lower alkylsulfonyl group, a lower alkoxycarbonyl group, a lower alkylcarbonyl group or a phenyl group and n is 1 or 2; $R^{1d}$ is a lower alkoxy group or a halogen atom; and $R^{2d}$ is a lower alkoxy group.

(6) A compound of the formula (Ie)

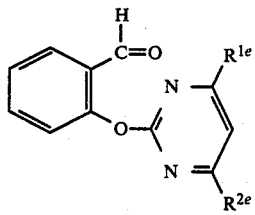

wherein $R^{1e}$ is a halogen atom, especially chlorine atom and $R^{2e}$ is a lower alkoxy group.

(7) A compound of the formula (If)

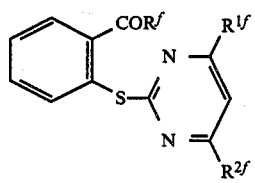

wherein $R^f$ is a hydroxy group, a lower alkoxy group or a group of the formula —OM where M is a cation of an alkali metal or an alkaline earth metal, or an ammonium $R^{1f}$ is a halogen atom, especially chlorine or a lower alkoxy group; and $R^{2f}$ is a lower alkoxy group.

(8) A compound of the formula (Ig)

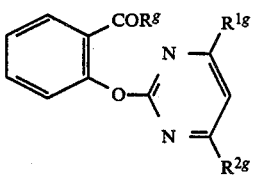

wherein $R^g$ is a hydroxy group or a lower alkoxy group, $R^{1g}$ is a halogen atom or a lower alkoxy group, and $R^{2g}$ is a halo-lower-alkyl group.

(9) A compound of the formula (Ih)

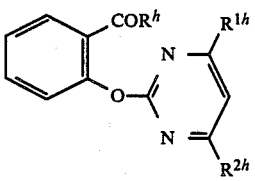

wherein $R^h$ is a chlorophenoxy group, a lower alkylphenoxy group, a di-lower-alkylphenoxy group or a lower-alkoxyphenoxy group, and $R^{1h}$ and $R^{2h}$ are each a lower alkoxy group.

(10) A compound of the formula (Ii)

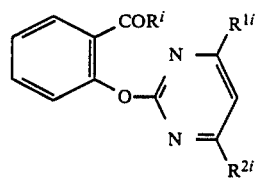

wherein $R^i$ is a lower alkoxy group, a trifluoromethyl-lower alkoxy group, a phenylthio group, or a furylmethoxy group, $R^{1i}$ is a methanesulfonylmethyl group or a lower alkoxy group, and $R^{2i}$ is a lower alkoxy group, a trifluoromethylphenoxyphenoxy group, a methylphenoxy group or a di-methylphenoxy group.

(11) A compound of the formula (Ij)

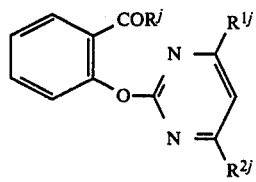

wherein $R^j$ is a hydroxy group, a lower alkoxy group or a benzyloxy group, $R^{1j}$ is a chlorine atom or a difluoromethoxy group, and $R^{2j}$ is a trifluoromethylmethoxy group or a difluoromethoxy group.

Amongst the new compounds of the formula (I) of the first aspect invention, the under-mentioned compounds are most preferred ones.

(1) 2-(4',6'-dimethoxypyrimidine-2'-yl)oxy-benzoic acid (2) Methyl 2-(4',6'-dimethoxypyrimidine-2'-yl)oxybenzoate (3) Ethyl 2-(4',6'-dimethoxypyrimidine-2'-yl)oxy-benzoate (4) n-Propyl 2-(4',6'-dimethoxypyrimidine-2'-yl)oxy-benzoate (5) Sodium 2-(4',6'-dimethoxypyrimidine-2'-yl)oxy-benzoate (6) Calcium bis [2-(4',6'-dimethoxypyrimidine-2'-yl)oxy]benzoate (7) 2-(4',6'-dimethoxypyrimidine-2'-yl)thio-benzoic acid.

According to a second aspect of this invention, there is provided a herbicidal composition comprising a herbicidally effective amount of a compound of the formula (I) as defined hereinbefore or a salt of said compound as the active ingredient, in association with a conventional carrier or diluent for the active ingredient.

When the new compound of the formula (I) according to this invention is used as a herbicidal agent, it may be applied to as such or in the form of a composition or formulation comprising the new compound of this invention as the active ingredient, in combination with a carrier for the active ingredient, optionally together with one or more of the other conventional additives such as surface-active agent, dispersing agent and auxiliary agents. The herbicidal composition may be formulated into various forms such as wettable powder, granules, powder, emulsifiable concentrate, emulsion, dispersion, solution, and the like.

Examples of the carrier which are available for the formulation of the herbicidal composition include solid carriers such as talc, bentonite, clay, kaoline, diatomaceous earth, white carbon (silica), vermiculite, slaked lime, siliceous sand, ammonium sulfate, urea and the like, as well as liquid carriers such as isopropyl alcohol, xylene, cyclohexane and the like. Suitable examples of the surface-active agent and the dispersing agent include esters of the sulfuric acid with alcohols, alkylsulfonic acid salts, lignin-sulfonic acid salts, polyoxyethylene glycol, ethers, polyoxyethylene alkylaryl ethers, polyoxyethylene sorbitain mono-alkylates and the like. The auxiliary agent may be, for example, carboxymethylcellulose (CMC), polyethylene glycol, gum arabic and the like. For practical use, the herbicidal composition of this invention may be applied directly as such or applied after the composition has been diluted with e.g. water to a suitable concentration of the active compound. The herbicidal composition of this invention may also contain and be applied together with one or more of the other herbicidal compounds.

The herbicidal compound or composition according to this invention may be used as a pre-emergence or post-emergence herbicidal agent. More particularly, the herbicidal compound or composition of this invention is effective to control or kill many kinds of weeds predominant in irrigated fields of aquatic rice plants, by treating the soil of the irrigated field with the herbicidal compound or composition, either before or after the weeds germinate. Further, the herbicidal compound or composition of this invention is effective to control or kill many kinds of weeds predominant in plowed fields and other non-irrigated agricultural fields, by treating the soil of such fields or the foliage of the weeds with the herbicidal compound or composition, either before or after the weeds germinate. Thus, the herbicidal compound or composition according to this invention may be applied directly onto the foliage of the weeds to be controlled and may also be applied to the soil where the weeds will grow or have grown.

The herbicidal compound or composition of this invention may usually be applied at a rate of application of the active compound in a range of 1 g to 1 Kg per 10 ares, preferably 5–500 g per 10 ares, upon the herbicidal treatment of the soil or the foliage of the weeds. Upon the herbicidal treatment of the foliage of the weeds, a diluted formulation containing the active compound at a concentration of 10 ppm. to 10,000 ppm. may preferably be applied to the leave of the weeds.

The herbicidal compound or composition according to this invention is advantageously able to control or kill effectively a wide variety of annual weeds such as barnyard grass (*Echinochloa crus-galli*), umbrella plant (flatsedge) (*Cyperus difformis*), monochoria (*Monochoria vaginalis*), bulrush (*Scirpus hotarui*), and "Hera-o-modaka" in Japanese (*Alisma canaliculatum*); a variety of perennial weeds such as "Mizugayaturi" in Japanese (*Cyperus serotinus*), "u-rikawa" in Japanese (*Sagittaria pygmaea*), "kuroguwai" in Japanese (*Eleocharis kuroguwai*), which annual weeds and perennial weeds predominantly grow in the irrigated fields of aquatic rice plants. The herbicidal compound or composition according to this invention is also able to control or kill effectively a wide variety of annual weeds such as barnyard grass (*Echinochloa crus-galli*), goose grass (*Eleusine indica*), green foxtail (*Setaria viridis*), water foxtail (*Alopecurus aequalis*), wild oat (*Avena fatua*), Italian ryegrass (*Lolium multiflorum*), smartgrass (*Polygonum lapathifolium*), slender amarauth (*Amaranthus viridis*), lambsquater ("Shiroza" in Japanese) (*Chenopodium album*), "Akaza" in Japanese (*Chenopodium album var. centrorubrum*), velvet leaf (*Abrilon theophrasti*), prickly sida (*Sida spinosa*), sicklepod (*Cassia tora*), common chickweed (*Stellaria media*), morningglory (*Ipomoea spp*), common cocklebur (*Xanthium strumarium*), and rice flatsedge (*Cyperus iria*); as well as perennial weeds such as purple nutsedge (*Cyperus rotundus*), Johnsongrass (*Sorghum halepense*), bermudagrass (*Cynodon dactylon*) and quackgrass (*Agropyron repens*), which annual weeds and perennial weeds predominantly grow in plowed farm fields (nonirrigated). In addition, the herbicidal compound or composition of this invention is of no or little pytotoxicity to the crop plants. Besides, advantageously, the herbicidal compound of the formula (I) according to this invention can show remarkably higher herbicidal activities against the perennial weeds, including purple nutsedge and Johnsongrass, as compared with the known compound as disclosed in the aforesaid Japanese patent application first publication "Kokai" No. 55729/79.

According to a third aspect of this invention, therefore, there is provided a method of combating or killing annual and perennial weeds in the fields of crop plants, which comprises applying a herbicidally effective amount of a compound of the formula (I) as shown hereinbefore, to the weeds or the area where the weeds will grow or have grown.

The production of the new pyrimidine derivatives of the formula (I) according to this invention is now described.

The new compound of the formula (I) according to this invention may be produced by any of the processes (A), (B), (C) and (D) as described below:

(1) According to the process (A), the compounds of the general formula (I) may be produced by reacting a compound of the formula (1) with a compound of the formula (2) given below, as depicted by the following reaction equation:

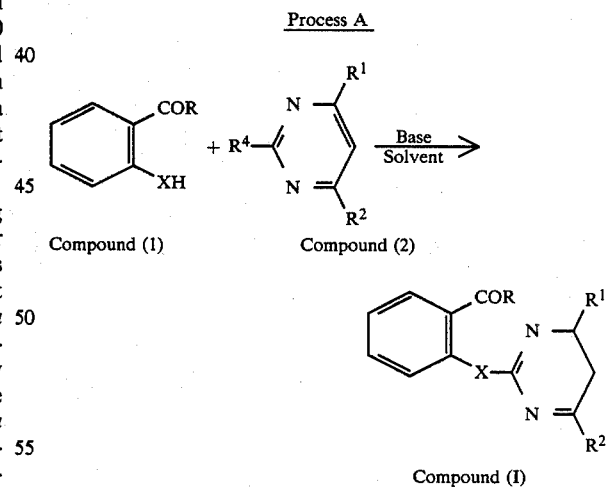

where R, X, $R^1$ and $R^2$ have the same meanings as defined hereinbefore for the formula (I) and $R^4$ denotes a leaving group such as a halo group, an alkylsulfonyl group, a benzylsulfonyl group or a substituted benzylsulfonyl group.

In accordance with the present process (A), the new compound of the formula (I) according to this invention may be prepared by reacting a compound of the formula (1) with a pyrimidine compound of the formula (2) in an inert organic solvent for 1 to 24 hours in the presence of a basic compound acting as an acid-binder and at a temperature of from room temperature to the refluxing temperature of the solvent as employed. The solvents available in this process (A) may be hydrocarbons such as benzene, toluene and xylene; halogenated hydrocarbons such as methylene chloride and chloroform; alcohols such as methanol, ethanol and isopropanol; ethers such as ethyl ether, isopropyl ether, tetrahydrofuran and 1,4-dioxane; ketones such as acetone and methyl ethyl ketone; esters such as methyl acetate and ethyl acetate; aprotic, polar organic solvents such as dimethylformamide, dimethylacetamide and dimethylsulfoxide; acetonitrile and water. The basic compounds available in this process (A) may be an alkali metal such as metallic sodium and metallic potassium; an alkaline metal hydride such as sodium hydride; an alkaline earth metal hydride such as calcium hydride; an alkali metal carbonate such as sodium carbonate and potassium carbonate; and an alkali metal hydroxide such as sodium hydroxide and potassium hydroxide.

(2) According to the process (B), some members of the compounds of the general formula (I) according to this invention may be produced by hydrolyzing a compound of the formula (3) under alkaline conditions and then optionally hydrolysing the hydrolysis product of the formula (4a) as formed, under acidic conditions, as depicted by the following reaction equations:

refluxing temperature of the reaction medium, to give the hydrolysis product of the formula (4a). When this product of the formula (4a) is further hydrolyzed in a known manner under acidic conditions, there is prepared a compound of the formula (4b) which is a free carboxylic acid form amongst the compounds of the formula (I) according to this invention.

The solvents available in this process (B) may be, for example, alcohols such as methanol, ethanol and isopropanol; and ketones such as acetone and methyl ethyl ketone. The available basic compounds may be an alkali metal or alkaline earth metal carbonate such as sodium carbonate, potassium carbonate and calcium carbonate; an alkali metal hydroxide such as sodium hydroxide and potassium hydroxide.

(3) According to the process (C), further some members of the compounds of the general formula (I) according to this invention may be produced by reacting the compound of the formula (4b) as formed in the aforesaid process (B) with an imidazolyl or chloride compound (G) identified below, to afford a compound of the formula (5) given below, which is, if desired, then reacted with an alcohol compound of the formula $R^5H$ to give a compound of the formula (3), as depicted by the following reaction equations:

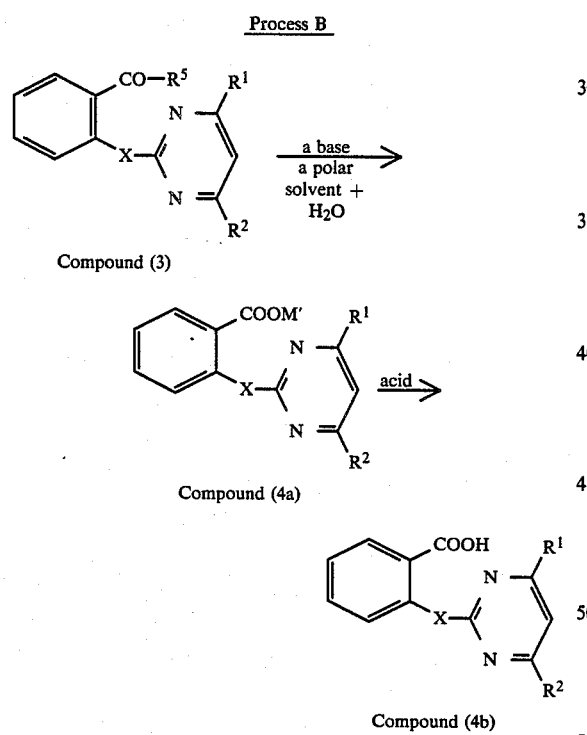

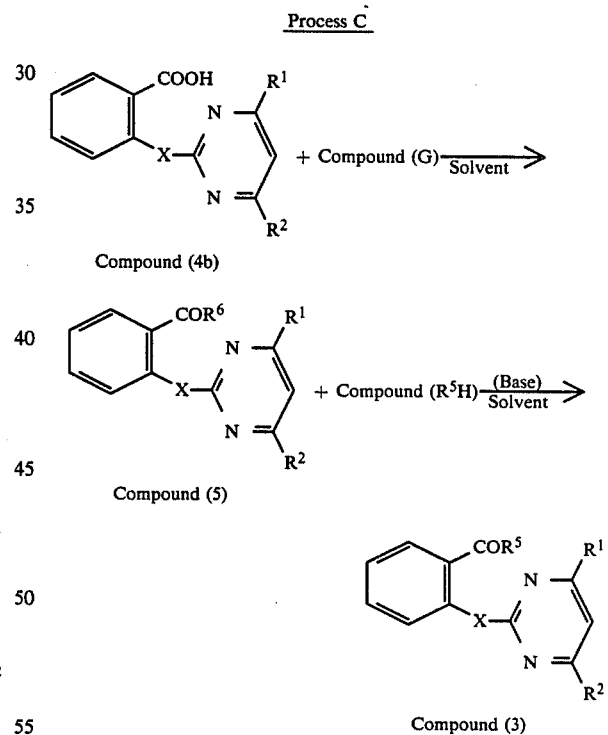

where $R^1$, $R^2$ and X are as defined above; $R^5$ is the same as defined above for the group R, except the hydrogen atom and hydroxy group; and M' is an alkaline metal or an alkaline earth metal.

In this process (B), the compounds of the formula (4a) in the form of the carboxylate according to this invention may be prepared by hydrolyzing a compound of the formula (3) in a polar organic solvent or in water, or in a mixture of a polar organic solvent and water in the presence of a basic compound of an alkali metal or alkaline earth metal. This hydrolysis reaction under alkaline conditions may be carried out for 0.5 to 36 hours at a temperature of from room temperature to the where $R^1$, $R^2$, X and $R^5$ are as defined above; and $R^6$ is an imidazolyl group or a chlorine atom.

In this process (C), the compound of the formula (5) may be prepared by reacting the compound of the formula (4b) with the imidazolyl or chloride compound (G) for 1 to 12 hours in an organic solvent at a temperature of from room temperature to the refluxing temperature of the solvent used.

The compound (G) to be used in this process (C) includes N,N'-carbonyldiimidazole, thionyl chloride, oxalic acid dichloride and phosgene. The solvents available in this process (C) may be, for example, hydrocarbons such as benzene, toluene and xylene; halogenated hydrocarbons such as methylene chloride and chloroform; ethers such as ethyl ether, isopropyl ether, tetrahydrofuran and 1,4-dioxane; ketones such as acetone and methyl ethyl ketone; and esters such as methyl acetate and ethyl acetate.

If desired, the compound of the formula (5) obtained may then be reacted with the alcohol compound of the formula $R^5H$ where $R^5$ is as defined hereinbefore, in an inert organic solvent, optionally in the presence of a basic compound. This reaction may be carried out for 0.5 to 12 hours either under ice-cooling or at a temperature of from room temperature to the boiling point of the solvent used, whereby the compound of the formula (3) is obtained. The solvents same as those just mentioned above may also be used for this reaction, and the basic compound may be selected from ordinary organic amines and inorganic bases which are conventionally used as the acid-binders.

(4) According to the process (D), another members of the compound of the formula (I) according to this invention may be prepared by reacting a halo compound of the formula (6) with an alkanol of the formula $R^7H$ where $R^7$ is a lower alkoxy group, in the presence of an acid-binder such as sodium hydroxide or carbonate, to give an alkoxy compound of the formula (7), as depicted by the following reaction equation:

Process D

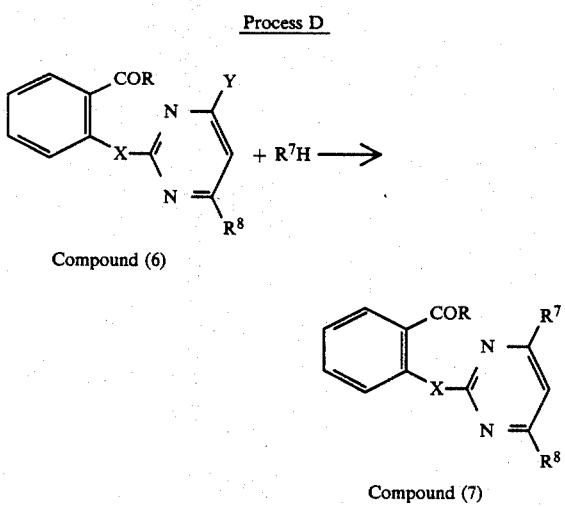

Compound (6)

Compound (7)

where R is as defined above; Y is a halogen atom such as chlorine; $R^7$ is an alkoxy group, and $R^8$ is same as the group $R^2$ except the halogen atom.

In the process (D), an alkali metal alkoxide such as sodium methoxide may be used as a reactive equivalent of the alkanol $R^7H$.

This invention is now illustrated with reference to the following Examples.

EXAMPLE 1

Preparation of methyl 2-(4'-methoxy-6'-methylpyrimidine-2'-yl)oxy-benzoate (Compound No. 16) (Process A)

A mixture of 2-benzylsulfonyl-4-methoxy-6-methylpyrimidine (5.0 g), methyl salicylate (2.8 g), methyl ethyl ketone (80 ml) and anhydrous potassium carbonate (25 g) was stirred for 3 hours under refluxing. The resulting reaction mixture was diluted with water and the aqueous mixture was extracted with chloroform. The chloroform extract was washed with water, dried and distilled under reduced pressure to remove the solvent therefrom, affording a pale yellow oil. The pale yellow oil was purified by chromatography on a column of silica gel. The titled compound was thus obtained as a colorless viscous liquid (3.2 g) having a refractive index of $n_D^{20}$ 1.5561.

EXAMPLE 2

Preparation of 2-(4'-chloro-6'-methoxypyrimidine-2'-yl)oxy benzoic acid (Compound No. 3) (Process B)

To a mixture of methanol (30 ml), water (30 ml) and sodium hydroxide (0.25 g) was added in small portions methyl 2-(4'-chloro-6'-methoxypyrimidine-2'-yl)oxybenzoate (1.9 g). The resulting mixture was stirred at room temperature for 1.5 hours. The reaction mixture was then distilled under reduced pressure to remove the methanol therefrom. The residual solution was adjusted to pH 2–3 by the addition of 5% aqueous hydrochloric acid, and a precipitate deposited immediately. The solid precipitate was recovered by filtration, washed with water (100 ml) and dried to give a free carboxylic acid product (1.5 g).

This product was recrystallized from isopropylether to afford a purified product of the titled compound (1.3 g) which showed a melting point of 149°–152° C.

EXAMPLE 3

Preparation of S-ethyl 2-(4',6'-dimethoxypyrimidine-2'-yl)oxy-benzothioate (Compound No. 25)(Process C)

N,N'-carbonyldiimidazole (2.5 g) was added in small portions to a mixture of 2-(4',6'-dimethoxypyrimidine-2'-yl)oxybenzoic acid (4.0 g) and tetrahydrofurane (80 ml). The resulting mixture was stirred for 2 hours under refluxing. The reaction mixture was cooled to a room temperature and then admixed with ethylmercaptan (2.6 g) and anhydrous potassium carbonate (2.1 g). The resulting mixture was stirred at room temperature for 5 hours. The reaction mixture was then diluted with water and the aqueous mixture was extracted with toluene. The toluene extract was washed with water, dried and distilled under reduced pressure to remove the solvent therefrom, giving a pale yellow solid. The solid was recrystallized from n-hexane to afford a purified product of the titled compound (3.8 g) which showed a melting point of 75°–77° C.

EXAMPLE 4

Preparation of sodium 2-(4'-chloro-6'-methoxypyrimidine-2'-yl)oxybenzoate (Compound No. 44)

2-(4'-chloro-6'-methoxypyrimidine-2'-yl)oxybenzoic acid (2.5 g) was added gradually to a mixture of methanol (50 ml) and sodium hydroxide (0.37 g). The resulting mixture was stirred at room temperature for 1 hour, and distilled under reduced pressure to remove the methanol therefrom, yielding a pale yellow solid product. The solid product was washed with ethyl ether and then with n-hexane, and dried to afford the titled compound (1.8 g) having a melting point of 196°–200° C. (with decomposition).

EXAMPLE 5

Preparation of methyl 2-(4'-methoxy-6'-isopropoxypyrimidin-2'-yl)oxybenzoate (Compound No. 23) (Process D)

To a solution of methyl 2-(4'-chloro-6'-isopropoxypyrimidin-2'-yl)oxybenzoate (4.0 g) in methanol (50 ml) was added a methanolic solution of 29% sodium methylate (2.4 g). The resulting mixture was stirred for 8 hours under refluxing. The reaction solution was distilled under reduced pressure to remove the methanol therefrom, and the residue was diluted with water.

The aqueous mixture obtained was extracted with toluene. The toluene extract was washed with water, dehydrated and distilled under reduced pressure to remove the solvent therefrom. A reddish brown oil was obtained. The oil was purified by chromatography on a column of silica gel, to obtain the titled compound as a colorless viscous liquid (1.7 g) having a refractive index of $n_D^{20}$ 1.5382.

By a procedure similar to the Example 1 above, there were further produced Compound Nos. 67 to 70 as indentified below.

| Compound Nos. | Formula | Properties |
| --- | --- | --- |
| 67 | [structure with COOCH₃, CH₂SO₂CH₃, OCH₃] | Colorless, thick-honey-like syrup. $n_D^{20}$ not measurable |
| 68 | [structure with COOCH₃, Cl, CH₂Cl] | Colorless, clear and viscous liquid $n_D^{20}$ 1.5835 |
| 69 | [structure with COOCH₃, OCH₃, CH₂Cl] | Colorless, clear and viscous liquid $n_D^{20}$ 1.5678 |
| 70 | [structure with COOCH₃, Cl, OCH₂CF₃] | Colorless needles mp. 80–81° C. |

The formulation of the herbicidal composition according to this invention is now illustrated by the following Examples 6–9, to which this invention is not limited. In these Examples, parts are given by weight, except otherwise stated.

EXAMPLE 6

Preparation of wettable powder

Compound No. 2 (10.0 parts), "Emulgen" 810 (a surface active agent comprising polyoxyethylene alkylaryl ether available commercially from KAO Co. Ltd., Japan) (0.5 parts), "Demol" N (a product comprising sodium β-naphthalene sulfonate polymer commercially available from KAO Co. Ltd., Japan) (0.5 parts), "Kunilite" 201 (a carrier comprising diatomaceous earth commercially available from Kunimine Industry Co. Ltd., Japan) (20.0 parts) and "Zieclite" CA (a carrier comprising clay commercially available from Zieclite Co. Ltd., Japan) (69.0 parts) were mixed together uniformly and ground finely to prepare a wettable powder containing 10% of the active compound.

EXAMPLE 7

Preparation of wettable powder

Compound No. 6 (10.0 parts), "Emulgen" 810 (0.5 parts), "Demol" N (0.5 parts), "Kunilite" 201 (20.0 parts), "Carplex" 80 (a carrier comprising silicone oxide, commercially available from Shionogi Seiyaku Co. Ltd., Japan) (5.0 parts) and "Zieclite" CA (64.0 parts) were mixed together uniformly and ground finely to prepare a wettable powder containing 10% of the active compound.

EXAMPLE 8

Preparation of emulsifiable concentrate

Compound No. 18 (30.0 parts), a mixture of xylene and isophorone (1:1 by volume) (60.0 parts) and a surfaceactive agent, "Sorpol" 800A (a surface active agent commercially available from TOHO Chemical Industry Co. Ltd., Japan) (10.0 parts) were mixed together homogeneously to prepare an emulsifiable concentrate (100.0 parts).

EXAMPLE 9

Preparation of granules

Compound No. 25 (10.0 parts), a mixture of talc and bentonite (1:3) (80.0 parts), white carbon (5.0 parts) and "Sorpol" N 800A (5.0 parts) were kneaded uniformly together with water (10.0 parts) to prepare a paste. The paste was extruded through a sieve (having meshes of 0.7 mm in diameter) and the extruded strands were dried and then cut into lengths of 0.5 to 1.0 mm each, to obtain the granules (100.0 parts).

The following Test Examples demonstrate the herbicidal activity of the herbicidal compounds of the formula (I) according to this invention.

TEST EXAMPLE 1

Each of pots was packed with a form soil. In the surface layer of the soil in each pot were planted at the depth of 1.0–1.5 cm tubers of purple nutsedge (*Cyperus rotundus*) and rootstocks of Johnsongrass (*Sorghum halepense*), and the soil in the pots was supplied with water. A predetermined amount of the wettable powder as prepared according to the Example 6 above was mixed and diluted with a proper volume of water to give an aqueous formulation containing a desired concentration of the active ingredient. One day after the supply of water to the soil, the aqueous formulation prepared as above was applied to the soil, by spraying uniformly over the soil surface at a rate of 1000 l per hectare, to effect the pre-emergence herbicidal treatment of the soil (A). On the other hand, the tubers of purple nutsedge and rootstocks of Johnsongrass as planted in the soil in the other pots were kept for 2 weeks in a glass greenhouse to allow the plants to grow. The predetermined amount of the wettable powder as prepared in the Example 6 above was diluted with a proper volume of water containing 2000 ppm. of "Surfactant W.K" (a product comprising polyoxyethylene dodecyl ether, sold from KAO Co.,Ltd. Japan) as the spreading agent, to prepare an aqueous formulation. This aqueous formulation prepared was sprayed uniformly over the foliage of the test weeds as grown, at a rate of 1000 l per hectare, to effect the post-emergence herbicidal treatment of the weed foliage (B).

The herbicidal effects on the weeds were evaluated by observing the overground segments of the weeds at the end of 30 days after the application of the herbicidal formulation, for the post-emergence herbicidal treatment of the foliage (B) and also for the pre-emergence herbicidal treatment of the soil (A) before the weeds germinate. The herbicidal effects so evaluated were assessed on the scales as described below:

| Scales for evaluation of the herbicidal effects | Rate of kill of weeds |
| --- | --- |
| 0 | No kill |
| 1 | Less than 30% |
| 2 | 30% to less than 50% |
| 3 | 50% to less than 70% |
| 4 | 70% to less than 90% |
| 5 | Not less than 90% |

The test results obtained are shown in Table 2 below.

TABLE 2

| Test Compound No. | Rate of Application of Active ingredient (Kg/ha) | Treatment of Soil (A) | | Treatment of Foliage (B) | |
| --- | --- | --- | --- | --- | --- |
| | | Cyp | Sor | Cyp | Sor |
| 2 | 4 | 4 | 5 | 5 | 5 |
| | 2 | 3 | 5 | 4 | 5 |
| | 1 | 3 | 5 | 4 | 5 |
| 4 | 4 | 5 | 5 | 5 | 5 |
| | 2 | 5 | 5 | 4 | 5 |
| | 1 | 5 | 5 | 4 | 5 |
| 6 | 4 | 3 | 5 | 3 | 4 |
| | 2 | 2 | 5 | 3 | 3 |
| | 1 | 1 | 2 | 3 | 3 |
| 17 | 4 | 5 | 5 | 5 | 5 |
| | 2 | 5 | 5 | 5 | 5 |
| | 1 | 5 | 5 | 5 | 5 |
| 18 | 4 | 5 | 5 | 4 | 5 |
| | 2 | 5 | 5 | 4 | 5 |
| | 1 | 5 | 5 | 3 | 5 |
| 19 | 4 | 5 | 5 | 5 | 5 |
| | 2 | 5 | 5 | 4 | 5 |
| | 1 | 4 | 5 | 4 | 5 |
| 21 | 4 | 5 | 5 | 4 | 5 |
| | 2 | 5 | 5 | 4 | 5 |
| | 1 | 4 | 5 | 4 | 5 |
| 25 | 4 | 5 | 5 | 5 | 5 |
| | 2 | 4 | 5 | 5 | 5 |
| | 1 | 4 | 5 | 5 | 5 |
| 26 | 4 | 5 | 5 | 5 | 5 |
| | 2 | 5 | 5 | 5 | 5 |
| | 1 | 5 | 5 | 5 | 5 |
| 27 | 4 | 5 | 5 | 5 | 5 |
| | 2 | 5 | 5 | 5 | 5 |
| | 1 | 5 | 5 | 5 | 5 |
| 29 | 4 | 5 | 5 | 5 | 5 |
| | 2 | 5 | 5 | 5 | 5 |
| | 1 | 5 | 5 | 5 | 5 |
| 32 | 4 | 5 | 5 | 5 | 5 |
| | 2 | 5 | 5 | 4 | 5 |
| | 1 | 4 | 5 | 4 | 5 |
| 33 | 4 | 5 | 5 | 5 | 5 |
| | 2 | 4 | 5 | 5 | 5 |
| | 1 | 4 | 5 | 5 | 5 |
| 34 | 4 | 5 | 5 | 5 | 5 |
| | 2 | 5 | 5 | 4 | 5 |
| | 1 | 5 | 5 | 4 | 4 |
| 35 | 4 | 4 | 5 | 5 | 5 |
| | 2 | 4 | 5 | 5 | 5 |
| | 1 | 3 | 5 | 5 | 5 |
| 37 | 4 | 5 | 5 | 5 | 5 |
| | 2 | 5 | 5 | 5 | 5 |
| | 1 | 4 | 5 | 5 | 5 |
| 40 | 4 | 5 | 5 | 4 | 5 |
| | 2 | 5 | 5 | 4 | 5 |
| | 1 | 5 | 5 | 3 | 5 |
| 41 | 4 | 5 | 5 | 3 | 5 |
| | 2 | 5 | 5 | 3 | 5 |
| | 1 | 4 | 5 | 2 | 5 |
| 45 | 4 | 5 | 5 | 5 | 5 |
| | 2 | 5 | 5 | 5 | 5 |
| | 1 | 5 | 5 | 4 | 5 |
| 46 | 4 | 5 | 5 | 5 | 5 |
| | 2 | 5 | 5 | 5 | 5 |
| | 1 | 5 | 5 | 5 | 5 |
| 47 | 4 | 5 | 5 | 5 | 5 |
| | 2 | 5 | 5 | 5 | 5 |
| | 1 | 5 | 5 | 5 | 5 |
| Comparative compound | 4 | 2 | 2 | 2 | 1 |
| | 2 | 1 | 0 | 1 | 1 |
| | 1 | 0 | 0 | 0 | 0 |

Notes:
In Table 2 above, abbreviations of the weeds under test denote the plants mentioned below:
Cyp: purple nutsedge (*Cyperus rotundus*)
Sor: Johnsongrass (*Sorghum halepense*)

The "Comparative" compound shown in Table 2 was the compound of the formula:

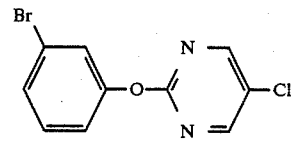

This compound is disclosed in the Japanese patent application first publication No. 55729/79. (This compound was used as the "comparative" compound also in Table 3 given hereinafter).

TEST EXAMPLE 2

Each of pots was packed with a form soil. In the surface layer of the soil in each of pots were planted at the depth of 0.5–1.5 cm tubers of purple nutsedge and rootstocks of Johnsongrass. Also, seeds of each of barnyard grass (*Echinochloa cruss-galli*), crab grass (*Digitaria sanguinalis*), smart weed (*Polygonum lapathifolium*), velvet leaf (*Abtilon theophrasti*), devils beggarticks (*Bidens frondosa*), wild morningglory (*Ipomoea spp*), peanut (*Arachis hypogaea*) and sunflower (*Helianthus annus*) were sown at the depth of 0.5 to 1.5 cm in the soil surface layer in each pot. The pots were fed with water. A predetermined amount of the wettable powder as prepared according to the Example 6 was mixed and diluted with water to prepare an aqueous formulation containing the active compound at a desired concentration. On the next day after the feed of water, the aqueous formulation prepared was applied to the soil by spraying uniformly over the surface of the soil at a rate of 1000 l per hectare to effect the pre-emergence herbicidal treatment of the soil.

The herbicidal effects on the weeds were evaluated by observing the overground segments of the weeds as grown at the end of 30 days after the application of the herbicidal formulation. The herbicidal effects on the weeds were assessed in term of the same scales as in the Test Example 1 above, and the phytotoxicity to crop plants was assessed according to the following gradings:

| Gradings for evaluation of the phytotoxicity to crop plants | Degree of damage of crop plants |
|---|---|
| 0 | No damage |
| 1 | Exceeding 0% but less than 30% |
| 2 | 30% to less than 50% |
| 3 | 50% to less than 70% |
| 4 | 70% to less than 90% |
| 5 | Not less than 90% (including complete kill) |

The test results obtained are shown in Table 3 below.

TABLE 3

| Test Compound No. | Rate of application of active ingredient (Kg/ha) | Herbicidal effects | | | | | | | | Phytotoxicity to crop plant | |
|---|---|---|---|---|---|---|---|---|---|---|---|
| | | Cyp | Sor | Ech | Dig | Pol | Abt | Bid | Ipo | Ara | Hel |
| 4 | 2 | 5 | 5 | 5 | 5 | 5 | 4 | 3 | 4 | 1 | 0 |
| | 1 | 5 | 5 | 5 | 5 | 5 | 2 | 2 | 3 | 0 | 0 |
| | 0.5 | 4 | 5 | 5 | 5 | 5 | 2 | 1 | 1 | 0 | 0 |
| | 0.25 | 3 | 4 | 4 | 4 | 5 | 1 | 0 | 0 | 0 | 0 |
| 17 | 2 | 5 | 5 | 5 | 5 | 5 | 5 | 5 | 5 | 0 | 1 |
| | 1 | 5 | 5 | 5 | 5 | 5 | 5 | 5 | 5 | 0 | 0 |
| | 0.5 | 4 | 4 | 5 | 5 | 5 | 5 | 4 | 2 | 0 | 0 |
| | 0.25 | 4 | 4 | 5 | 5 | 5 | 5 | 4 | 1 | 0 | 0 |
| 18 | 2 | 5 | 5 | 5 | 5 | 5 | 3 | 0 | — | 1 | 0 |
| | 1 | 5 | 5 | 5 | 5 | 5 | 2 | 0 | — | 1 | 0 |
| | 0.5 | 4 | 5 | 5 | 5 | 5 | 2 | 0 | — | 0 | 0 |
| | 0.25 | 3 | 5 | 5 | 5 | 4 | 1 | 0 | — | 0 | 0 |
| "Comparative" compound | 2 | 3 | 0 | 5 | 5 | 2 | 5 | 0 | 0 | 0 | 0 |
| | 1 | 0 | 0 | 5 | 5 | 1 | 4 | 0 | 0 | 0 | 0 |
| | 0.5 | 0 | 0 | 5 | 5 | 0 | 0 | 0 | 0 | 0 | 0 |
| | 0.25 | 0 | 0 | 1 | 5 | 0 | 0 | 0 | 0 | 0 | 0 |

Notes:
In Table 3 above, abbreviations of the weeds under test denote the under-mentioned plants:
Cyp: purple nutsedge (*Cyperus rotundus*)
Sor: Johnson grass (*Sorghum halepense*)
Ech: barnyard grass (*Echinochloa cruss-galli*)
Dig: crag grass (*Digitaria sanguinalis*)
Pol: smart weed (*Polygonum nodusum*)
Abt: velvet leaf (*Abtilon theophrasti*)
Bid: devils beggarticks (*Bidens frondosa*)
Ipo: wild morning glory (*Ipomoea spp*)
Ara: peanut (*Arachis hypogaea*)
Hel: sunflower (*Helianthus annus*)

TEST EXAMPLE 3

Each of pots was packed with a farm soil. In the surface layer of the soil in each pot were sown at the depth of 0.5–1 cm seeds of each of barnyard grass (*Echinochloa cruss-galli*), crab grass (*Digitaria sanguinalis*), smart weed (*Polygonum nodusum*), slender amarauth (*Ameranthus viridis*), lambsquater (*Chenopodium album*) and rice flatsedge (*Cyperus iria*), and the pots were fed with water. An amount of the wettable powder prepared according to the Example 6 above was diluted with water to prepare an aqueous formulation containing the active ingredient compound at a desired concentration of 4 Kg/1000 l. On the next day after the sowing, the aqueous formulation as prepared was applied uniformly to the soil by spraying over the soil surface at a rate of 1000 l per hectare, and the pots were allowed to stand in a glass greenhouse. Thus, the pre-emergence herbicidal treatment of the soil was conducted. On the other hand, the seeds of the weeds sown in the soil in the other pots were kept in a glass greenhouse for 2 weeks to allow the weeds to grow. The same amount of the wettable powder prepared in the Example 6 above was diluted with water containing 2000 ppm. of "Surfactant W.K" as the spreading agent, and the aqueous formualtion thus prepared and containing the active compound at a concentration of 4 Kg/1000 l was applied uniformly onto the foliage of the weeds, by spraying at a rate of 1000 l per hectare. The pots treated were allowed to stand in a glass greenhouse. Thus, the post-emergence herbicidal treatment of the weed foliage was effected.

Evaluation of the herbicidal effects was made by observing the overground parts of the weeds on the 20th day after the application of the herbicidal formulation for the herbicidal treatment of the soil, but on the 14th day after the application of the herbicidal composition for the herbicidal treatment of the foliage of the weeds. The herbicidal effects were assessed in term of the same scales as in the Test Example 1.

The test results obtained are shown in Table 4 below.

TABLE 4

| Test Compound No. | Treatment of Soil | | | | | | Treatment of Foliage | | | | | |
|---|---|---|---|---|---|---|---|---|---|---|---|---|
| | Ech | Dig | Pol | Ama | Che | Cyp | Ech | Dig | Pol | Ama | Che | Cyp |
| 1 | 5 | 5 | 5 | 5 | 5 | 5 | 4 | 5 | 4 | 5 | 1 | 4 |
| 2 | 5 | 5 | 4 | 5 | 5 | 5 | 5 | 5 | 4 | 5 | 5 | 5 |
| 3 | 4 | 4 | 1 | 5 | 5 | 5 | 5 | 5 | 4 | 5 | 5 | 5 |
| 4 | 5 | 5 | 5 | 5 | 5 | 5 | 5 | 5 | 5 | 5 | 5 | 5 |
| 5 | 3 | 3 | 4 | 4 | 4 | 5 | 3 | 3 | 3 | 3 | 4 | 2 |
| 6 | 5 | 5 | 4 | 5 | 5 | 5 | 4 | 4 | 4 | 5 | 4 | 5 |
| 7 | 5 | 5 | 5 | 5 | 5 | 5 | 5 | 4 | 5 | 5 | 5 | 5 |
| 8 | 4 | 3 | 2 | 3 | 2 | 3 | 2 | 2 | 1 | 2 | 2 | 2 |
| 9 | 5 | 5 | 2 | 5 | 4 | 5 | 3 | 4 | 1 | 5 | 4 | 3 |
| 10 | 1 | 1 | 3 | 3 | 3 | 3 | 0 | 1 | 4 | 1 | 2 | 0 |
| 11 | 5 | 4 | 5 | 5 | 5 | 5 | 5 | 5 | 5 | 5 | 5 | 5 |
| 12 | 5 | 4 | 5 | 5 | 5 | 5 | 3 | 2 | 5 | 5 | 5 | 2 |
| 13 | 5 | 5 | 5 | 5 | 5 | 5 | 4 | 3 | 5 | 5 | 5 | 5 |
| 14 | 0 | 0 | 0 | 4 | 4 | 1 | 3 | 2 | 4 | 5 | 4 | 1 |
| 15 | 4 | 4 | 5 | 5 | 5 | 5 | 4 | 3 | 5 | 5 | 5 | 4 |
| 16 | 5 | 5 | 5 | 5 | 4 | 5 | 4 | 4 | 5 | 5 | 5 | 4 |
| 17 | 5 | 5 | 5 | 5 | 5 | 5 | 5 | 5 | 5 | 5 | 5 | 5 |
| 18 | 5 | 5 | 5 | 5 | 5 | 5 | 5 | 5 | 4 | 5 | 5 | 4 |
| 19 | 5 | 5 | 5 | 5 | 5 | 5 | 5 | 5 | 4 | 5 | 5 | 4 |
| 20 | 5 | 5 | 5 | 5 | 5 | 4 | 3 | 4 | 5 | 5 | 5 | 3 |
| 21 | 5 | 5 | 5 | 5 | 5 | 5 | 5 | 5 | 5 | 5 | 5 | 4 |
| 22 | 4 | 4 | 3 | 5 | 5 | 5 | 4 | 4 | 3 | 5 | 5 | 3 |
| 23 | 1 | 1 | 3 | 5 | 5 | 0 | 2 | 1 | 5 | 3 | 2 | 2 |
| 24 | 4 | 4 | 3 | 3 | 5 | 5 | 4 | 3 | 3 | 3 | 4 | 2 |
| 25 | 5 | 5 | 5 | 5 | 5 | 5 | 5 | 5 | 5 | 5 | 5 | 5 |
| 26 | 5 | 5 | 5 | 5 | 5 | 5 | 5 | 5 | 5 | 5 | 5 | 5 |
| 27 | 5 | 5 | 5 | 5 | 5 | 5 | 5 | 5 | 5 | 5 | 5 | 5 |
| 28 | 4 | 4 | 2 | 3 | 4 | 5 | 4 | 4 | 3 | 3 | 2 | 2 |
| 29 | 5 | 5 | 5 | 5 | 5 | 5 | 5 | 5 | 5 | 5 | 5 | 5 |
| 30 | 5 | 5 | 3 | 5 | 5 | 5 | 5 | 5 | 5 | 5 | 5 | 5 |
| 31 | 5 | 5 | 3 | 5 | 4 | 5 | 5 | 5 | 4 | 5 | 5 | 5 |
| 32 | 5 | 5 | 4 | 5 | 5 | 5 | 5 | 5 | 5 | 5 | 5 | 4 |
| 33 | 5 | 5 | 5 | 5 | 5 | 5 | 5 | 5 | 5 | 5 | 5 | 5 |
| 34 | 5 | 5 | 4 | 5 | 5 | 5 | 5 | 5 | 5 | 5 | 5 | 5 |
| 35 | 5 | 5 | 5 | 5 | 5 | 5 | 5 | 5 | 5 | 5 | 5 | 5 |
| 36 | 5 | 5 | 5 | 5 | 5 | 5 | 5 | 5 | 5 | 5 | 5 | 5 |
| 37 | 5 | 5 | 5 | 5 | 5 | 5 | 5 | 5 | 5 | 5 | 5 | 5 |
| 38 | 5 | 5 | 5 | 5 | 5 | 5 | 5 | 5 | 5 | 5 | 5 | 5 |
| 39 | 5 | 5 | 5 | 5 | 5 | 5 | 5 | 5 | 5 | 5 | 5 | 5 |
| 40 | 5 | 5 | 5 | 5 | 5 | 5 | 5 | 5 | 5 | 4 | 4 | 4 |
| 41 | 5 | 5 | 4 | 5 | 5 | 5 | 5 | 5 | 5 | 5 | 5 | 5 |
| 42 | 4 | 4 | 0 | 4 | 3 | 4 | 3 | 3 | 2 | 3 | 2 | 2 |
| 43 | 5 | 5 | 5 | 5 | 5 | 5 | 5 | 5 | 5 | 5 | 5 | 5 |
| 44 | 5 | 5 | 4 | 4 | 5 | 5 | 5 | 5 | 5 | 5 | 4 | 4 |
| 45 | 5 | 5 | 4 | 5 | 5 | 5 | 5 | 5 | 5 | 5 | 5 | 5 |
| 46 | 5 | 5 | 5 | 5 | 5 | 5 | 5 | 5 | 5 | 5 | 5 | 5 |
| 47 | 5 | 5 | 5 | 5 | 5 | 5 | 5 | 5 | 5 | 5 | 5 | 5 |
| 48 | 5 | 5 | 5 | 5 | 5 | 5 | 5 | 5 | 5 | 5 | 5 | 5 |
| 49 | 5 | 5 | 5 | 5 | 5 | 4 | 3 | 3 | 2 | 4 | 3 | 4 |
| 50 | 4 | 3 | 2 | 4 | 2 | 3 | 3 | 3 | 3 | 5 | 3 | 3 |
| 51 | 5 | 5 | 5 | 5 | 5 | 4 | 5 | 5 | 5 | 5 | 5 | 4 |
| 52 | 5 | 5 | 5 | 5 | 5 | 4 | 5 | 5 | 5 | 5 | 5 | 4 |
| 53 | 5 | 5 | 5 | 5 | 5 | 4 | 5 | 5 | 5 | 5 | 5 | 4 |
| 54 | 5 | 5 | 5 | 5 | 4 | 2 | 5 | 5 | 4 | 5 | 2 | 2 |
| 55 | 5 | 5 | 5 | 5 | 5 | 5 | 5 | 5 | 5 | 5 | 5 | 5 |
| 56 | 5 | 5 | 5 | 5 | 5 | 5 | 5 | 5 | 5 | 5 | 5 | 5 |
| 57 | 5 | 5 | 5 | 5 | 5 | 5 | 5 | 5 | 5 | 5 | 5 | 5 |
| 58 | 3 | 4 | 4 | 4 | 2 | 3 | 5 | 4 | 4 | 4 | 4 | 3 |
| 59 | 5 | 5 | 5 | 5 | 5 | 5 | 5 | 4 | 3 | 5 | 5 | 5 |
| 60 | 3 | 1 | 5 | 4 | 4 | 1 | 2 | 2 | 4 | 5 | 3 | 4 |
| 61 | 3 | 2 | 5 | 5 | 4 | 2 | 3 | 3 | 5 | 5 | 4 | 5 |
| 62 | 2 | 5 | 4 | 5 | 5 | 4 | 5 | 4 | 5 | 5 | 5 | 4 |
| 63 | 4 | 5 | 4 | 5 | 4 | 5 | 4 | 2 | 4 | 4 | 4 | 3 |
| 64 | 4 | 5 | 3 | 5 | 5 | 5 | 5 | 3 | 5 | 5 | 5 | 4 |
| 65 | 2 | 4 | 4 | 4 | 5 | 3 | 2 | 2 | 3 | 3 | 3 | 1 |

TABLE 4-continued

| Test Compound No. | Treatment of Soil | | | | | | Treatment of Foliage | | | | | |
|---|---|---|---|---|---|---|---|---|---|---|---|---|
| | Ech | Dig | Pol | Ama | Che | Cyp | Ech | Dig | Pol | Ama | Che | Cyp |
| 66 | 3 | 3 | 2 | 4 | 5 | 4 | 2 | 2 | 4 | 1 | 3 | 2 |

Notes:
In the Table 4, abbreviations of the test weeds denote the under-mentioned plants:-
Ech: barnyard grass (*Echinochloa cruss-galli*);
Dig: crabgrass (*Digitaria sanguinalis*);
Pol: smart weed (*Polygonum nodusum*)
Ama: slender amarauth (*Amaranthus viridis*);
Che: lambsquater (*Chenopodium album*);
Cyp: rice flatsedge (*Cyperus iria*)

TEST EXAMPLE 4

The test procedures of the Test Example 1 above were repeated using the tubers of purple nutsedge (*Cyperus rotundus*) and the test compounds as identified in Table 5 below.

The herbicidal effects obtained for the preemergence herbicidal treatment (A) and for the postemergence herbicidal treatment (B) of tubers of purple nutsedge were assessed on the same scales as given in the Test Example 1.

The test results obtained are summarized in Table 5 below.

TABLE 5

| Test compound No. | Rate of application of active ingredient (Kg/ha) | Treatment of Soil (A) Cyp | Treatment of Foliage (B) Cyp |
|---|---|---|---|
| 48 | 4 | 5 | 5 |
| | 2 | 5 | - |
| 51 | 4 | 5 | 4 |
| | 2 | 5 | - |
| 52 | 4 | 5 | - |
| | 2 | 5 | - |
| 53 | 4 | 5 | - |
| | 2 | 5 | - |
| 55 | 4 | 4 | - |
| | 2 | 4 | - |
| 56 | 4 | 5 | - |
| | 2 | 4 | - |
| 57 | 4 | 4 | 4 |
| | 2 | 4 | - |
| 59 | 4 | - | 5 |
| Comparative compound | 4 | 2 | 2 |
| | 2 | 1 | - |

Note:
In the Table 5, "Cyp" denotes purple nutsedge (*Cyperus rotundus*).
The hyphen "-" indicates that no test was conducted.
"Comparative compound" used was the same as that in the Test Example 1.

What we claim is:

1. A pyridine compound represented by the formula (I)

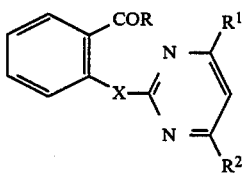

wherein R denotes a hydrogen atom or a hydroxy group or a lower alkoxy group, a lower alkylthio group, a lower alkenyloxy group, a lower alkynyloxy group, a phenoxy group, a chlorophenoxy group, a lower alkylphenoxy group, a di-lower-alklyphenoxy group, a lowe-ralkoxyphenoxy group, a phenylthio group, an isopropylideneaminoxy group, an imidazolyl group, a group of the formula —O—$(CH_2)_n$—$R^3$ is a halogen atom or a hydroxy group, a trifluoromethyl group, a lower alkoxy group, a lower alkylthio group, a lower alkylsulfonyl group, a lower alkoxycarbonyl group, a lower alkylcarbonyl group, a phenyl group or a furyl group; and n is an integer of 1 or 2, or R dentoes a group —OM where M is a cation of an alkali metal or alkaline earth metal or ammonium cation or an organic substituted ammonium cation of the formula —$NR^9R^{10}R^{11}R^{12}$—+ wherein $R^9$, $R^{10}$, $R^{11}$ and $R^{12}$ are each a hydrogen atom, a linear or branched ($C_1$-$C_6$) alkyl group, a ($C_1$-$C_6$) hydroxy alkyl group, a phenyl group or a benzyl group, and $R^1$ and $R^2$ are the same or different and each denotes a halogen atom or a lower alkyl group, a lower haloalkyl group, a lower alkxoy group, a lower alkylthio group, a mono-, di- or tri-halo-lower-alkoxy group, a di-lower-alkylamino group, a methanesulfonylmethyl group, a trifluoromethylphenoxyphenoxy group, a methylphenoxy group or a di-methylphenoxy group, and X is an oxygen atom or sulfur atom.

2. A compound as claimed in claim 1 in which $R^1$ and $R^2$ are each a lower alkoxy group.

3. A compound as claimed in claim 1 in which X is the oxygen atom.

4. A compound as claimed in claim 1 in which $R^1$ and $R^2$ are each a methoxy group.

5. A compound as claimed in claim 1 which is a compound of the formula

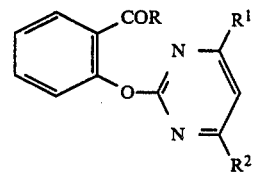

wherein R is a hydrogen atom or a hydroxy group, a lower alkoxy group, a lower alkylthio group, a lower alkenyloxy group, a lower alkynyloxy group, a phenoxy group or a group of the formula —O—$(CH_2)_n$—$R^3$ where $R^3$ is a halogen atom, a hydroxy group, a lower alkoxy group, a lower alkylthio group, a lower alkylsulfonyl group, a lower alkoxycarbonyl group, a lower alkylcarbonyl group, or a phenyl group; and n is an integer of 1 or 2; or R is a group of the formula —OM where M is a cation of an alkali metal, an alkaline earth metal or ammonium, or an organic substituted ammonium cation of the formula —$NR^9R^{10}R^{11}R^{12}$—+ wherein $R^9$, $R^{10}$, $R^{11}$ and $R^{12}$ are each a hydrogen atom, a linear or branched ($C_1$-$C_6$) alkyl group, a ($C_1$-$C_6$) alkoxy group, a phenyl group or a benzyl group, and $R^1$ and $R^2$ are each a halogen atom or a lower alkyl group, a lower alkoxy group, a lower alkylthio group, a halo-lower-alkoxy group or a di-lower-alkylamino group.

6. A pyrimidine compound as claimed in claim 1 which is a compound of the formula (Ia)

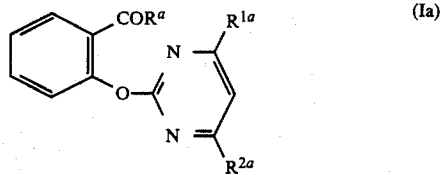

wherein $R^a$ is a hydroxy group, a lower alkoxy group, a lower alkenyloxy group, a lower alkynyloxy group or a group of the formula —OM where M is a cation of an alkali metal, an alkaline earth metal or an ammonium cation; and $R^{1a}$ and $R^{2a}$ are each a lower alkoxy group.

7. A pyrimidine compound as claimed in claim 1 which is a compound of the formula (Ib)

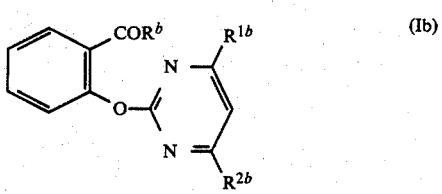

wherein $R^b$ is a hydroxy group or a lower alkoxy group; $R^{1b}$ is a halogen atom, particularly chlorine or fluorine atom, or a lower alkyl group, or a di-fluoro-lower-alkoxy group, and $R^{2b}$ is a lower alkyl group or a lower alkoxy group.

8. A pyrimidine compound as claimed in claim 1 which is a compound of the formula (Ic)

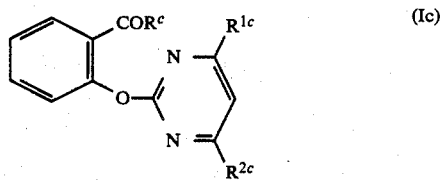

wherein $R^c$ is a lower alkoxy group, $R^{1c}$ is a di-loweralkylamino group or a lower alkylthio group, and $R^{2c}$ is a lower alkoxy group.

9. A pyrimidine compound as claimed in claim 1 which is a compound of the formula (Id)

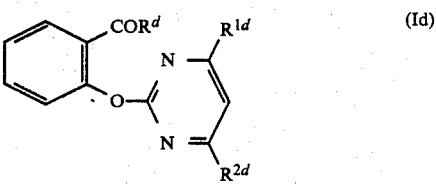

wherein $R^d$ is a lower alkylthio group, a phenoxy group, an isopropylideneaminoxy group, an imidazolyl group, or a group of the formula —O—(CH$_2$)$_n$—R$^3$ where R$^3$ is a halogen atom or a hydroxy group, a lower alkoxy group, a lower alkylthio group, a lower alkylsulfonyl group, a lower alkoxycarbonyl group, a lower alkylcarbonyl group or a phenyl group and n is 1 or 2; $R^{1d}$ is a lower alkoxy group or a halogen atom; and $R^{2d}$ is a lower alkoxy group.

10. A pyrimidine compound as claimed in claim 1 which is a compound of the formula (Ie)

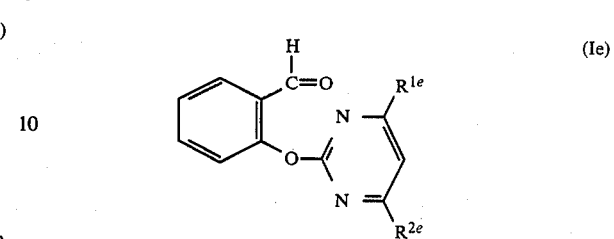

wherein $R^{1e}$ is a halogen atom, especially chlorine atom and $R^{2e}$ is a lower alkoxy group.

11. A pyrimidine compound as claimed in claim 1 which is a compound of the formula (If)

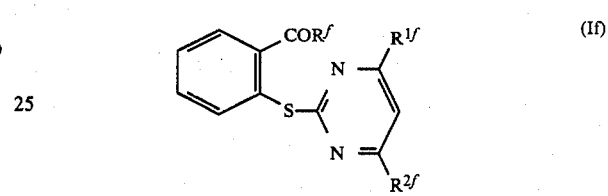

wherein $R^f$ is a hydroxy group, a lower alkoxy group or a group of the formula —OM where M is a cation of an alkali metal or an alkaline earth metal, or an ammonium cation $R^{1f}$ is a halogen atom, especially chlorine or a lower alkoxy group; and $R^{2f}$ is a lower alkoxy group.

12. A pyrimidine compound as claimed in claim 1 which is a compound of the formula (Ig)

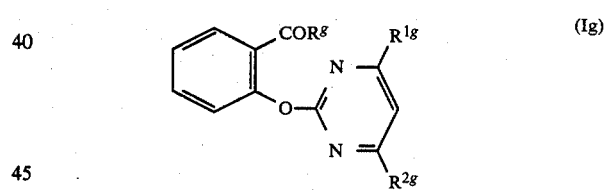

wherein $R^g$ is a hydroxy group or an alkoxy group, $R^{1g}$ is a halogen atom or a lower alkoxy group, and $R^{2g}$ is a lower haloalkyl group.

13. A pyrimidine compound as claimed in claim 1 which is a compound of the formula (Ih)

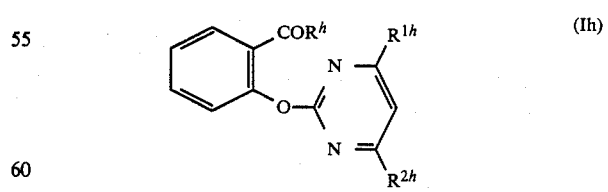

wherein $R^h$ is a chlorophenoxy group, a lower-alkylphenoxy group, a di-lower-alkylphenoxy group or a lower-alkoxyphenoxy group, and $R^{1h}$ and $R^{2h}$ are each a lower alkoxy group.

14. A pyrimidine compound as claimed in claim 1 which is a compound of the formula (Ii)

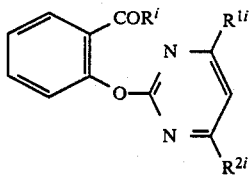

wherein $R^i$ is a lower alkoxy group, a trifluoromethyl-lower alkoxy group, a phenylthio group, or a furylmethoxy group, $R^{1i}$ is a methanesulfonylmethyl group or a lower alkoxy group, and $R^{2i}$ is a lower alkoxy group, a trifluoromethylphenoxyphenoxy group, a methylphenoxy group or a di-methylphenoxy group.

15. A pyrimidine compound as claimed in claim 1 which is a compound of the formula (Ij)

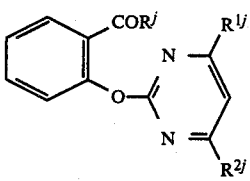

wherein $R^j$ is a hydroxy group, a lower alkoxy group or a benzyloxy group, $R^{1j}$ is a chlorine atom or a difluoromethoxy group, and $R^{2j}$ is a trifluoromethylmethoxy group or a difluoromethoxy group.

16. A pyrimidine compound as claimed in claim 1 or claim 6 which is selected from:
2-(4',6'-dimethoxypyrimidine-2'-yl)oxy-benzoic acid, methyl 2-(4',6'-dimethoxypyrimidine-2'-yl)oxybenzoate, ethyl 2-(4',6'-dimethoxypyrimidine-2'-yl)oxybenzoate, n-propyl 2-(4',6'-dimethoxypyrimidine-2'-yl) oxy-benzoate, sodium 2-(4',6'-dimethoxypyrimidine-2'-yl) oxy-benzoate, and calcium bis [2-(4',6'-dimethoxypyrimidine-2'-yl)oxy]-benzoate.

17. A pyrimidine compound as claimed in claim 1, which is 2-(4',6'-Dimethoxypyrimidin-2'-yl) thiobenzoic acid.

18. A pyrimidine compound as claimed in claim 1, which is n-Butyl-2-(4',6'-dimethoxypyrimidin-2'yl) oxybenzoate.

19. A herbicidal composition comprising an effective amount of a compound of the formula (I) as defined in claim 1 or a salt of said compound as the active ingredient, in association with a carrier or diluent for the active ingredient.

20. A method of combating or killing annual and perennial weeds in the fields of crop plants, which comprises applying a herbicidally effective amount of a compound of the formula (I) as defined in claim 1, to the weeds or the area where the weeds will grow or have grown.

* * * * *